United States Patent [19]
Robinson

[11] Patent Number: 5,167,694
[45] Date of Patent: Dec. 1, 1992

[54] FATTY ACID AND AMIDE WETTING AGENTS FOR PESTICIDE FORMULATIONS

[75] Inventor: Philip L. Robinson, Isle of Palms, S.C.

[73] Assignee: Westvaco Corporation, New York, N.Y.

[21] Appl. No.: 518,267

[22] Filed: May 4, 1990

Related U.S. Application Data

[63] Continuation-in-part of Ser. No. 298,676, Jan. 19, 1989, abandoned.

[51] Int. Cl.⁵ .................... A01N 43/48; A01N 43/64; A01N 43/36; A01N 37/00
[52] U.S. Cl. ............................................. 71/92; 71/95; 71/98; 71/100; 71/120; 71/DIG. 1; 252/355; 514/937; 514/942
[58] Field of Search .................. 252/355, 357, 311; 562/58; 71/64.08, DIG. 1, 92, 95, 98, 100, 120, 64.01, 64.03; 260/401; 514/942, 937

[56] References Cited

U.S. PATENT DOCUMENTS

| | | | |
|---|---|---|---|
| 3,029,250 | 4/1962 | Gaertner | 252/355 X |
| 3,342,581 | 9/1967 | Woodward et al. | 252/353 X |
| 3,575,883 | 4/1971 | Foley | 252/355 X |
| 3,615,798 | 10/1971 | Woodruff | 252/311.5 X |
| 3,649,543 | 3/1972 | Cahn et al. | 252/353 X |
| 3,986,979 | 10/1976 | Moorer et al. | 252/353 |
| 4,494,992 | 1/1985 | Schilling | 252/311.5 X |
| 4,547,224 | 10/1985 | Schilling | 252/311.5 X |
| 4,561,901 | 12/1985 | Schilling | 252/311.5 X |
| 4,618,450 | 10/1986 | Higgins | 252/355 |
| 4,786,720 | 11/1988 | Schilling | 260/401 X |

*Primary Examiner*—Robert L. Stoll
*Assistant Examiner*—Daniel S. Metzmaier
*Attorney, Agent, or Firm*—Terry B. McDaniel; Daniel B. Reece, IV; Richard L. Schmalz

[57] ABSTRACT

Disclosed are pesticide formulations containing oil-free chemical compositions as wetting agents and the oil-free wetting agents produced by reacting a tall oil fatty acid or ester with an anhydride compound and an amino sulfonic acid compound in water alone to produce an acid amide salt, an imide salt, or the adduct thereof.

9 Claims, No Drawings

FATTY ACID AND AMIDE WETTING AGENTS FOR PESTICIDE FORMULATIONS

This application is a continuation-in-part of application Ser. No. 07/298,676 filed Jan. 19, 1989, now abandoned.

BACKGROUND OF THE INVENTION (1) Field of the Invention

The present invention is directed to the production of wetting agents in pesticide formulations for use in agricultural applications. The invention is directed towards both method of manufacture, products produced and incorporation of said compositions into agricultural formulations thereby.

(2) Description of the Prior Art

Pesticide formulations used in agricultural formulations generally encompass herbicides, insecticides, fungicides, and rodenticides. The most popular forms of application of such formulations include emulsifiable concentrates, flowables, wettable powders, and water-dispersible granules. Emulsifiable concentrates are produced by dissolving the pesticide and the emulsifying agent in a water-insoluble organic solvent which is diluted with water at the time of use to form a stable suspension for spraying. Flowable formulations are dispersions of solid particles in a liquid, usually water, in which the solid has little or no solubility. A wetting agent concentration of around 2% is usually added to get the dry pesticide into the water phase for dispersion.

The wettable powder formulation is similar to the flowable formulations, except that the pesticides are pre-granulated with a dispersant and a wetting agent into small composite particles. The resulting small particle granules readily wet and disperse when added to water.

The water-dispersible granule formulations are formed by granulating mixtures of the pesticide with a wetting agent and a dispersant. A clay binder is often added to allow formation of large particles that can readily disintegrate and disperse in water.

In the past, a large majority of all pesticides were sold as emulsifiable concentrate formulations. Recently, however, with more governmental restrictive control imposed on unnecessary organic oils in pesticide formulations, water-dispersible granule formulations have been replacing the emulsifiable concentrate formulations. This greatly increases the market potential and demand for oil-free wetting agents and dispersants necessary for proper formulation of wettable powders or water-dispersible granules.

For example, U.S. Pat. No. 4,618,450 teaches amino sulfonic acid derivatives of carboxylic acids as emulsifiers, thickeners and dispersants in aqueous systems. Unfortunately, the products are themselves not oil-free, and the aqueous systems to which they are applied are taught to contain an oil phase ("diluent oil"). The present invention, on the other hand, is directed to oil-free wetting agents for application in aqueous systems with only a water phase.

Also, pesticide compositions have included lignin compositions as dispersants and napthylene sulfonates, ethoxylated alcohols, or tall oil fatty acid-derived materials as wetting agents. One such wetting agent product, a sulfonic acid derivative of tall oil fatty acid such as produced as a by-product of the kraft wood-pulping process, is taught in U.S. Pat. No. 3,986,979. Although compositions as this work acceptably as wetting agents, the reaction creates hydrogen chloride as a by-product, resulting in a highly corrosive atmosphere for reaction equipment, thereby reducing the life of the equipment.

SUMMARY OF THE INVENTION

The present invention is directed to an improved pesticide formulation resulting from superior wetting agents produced from tall oil fatty acid and fatty ester compounds by reacting a fatty acid anhydride or a fatty ester anhydride with an amino sulfonic acid salt in an oil-free aqueous medium over a pH range specific for the starting fatty acid or ester anhydride. Sufficient temperature is required to produce a fatty acid or fatty ester amido or imido reaction product with the sulfonic acid salt. When using as a wetting agent in dry pesticide formulations, the resultant product provides an improvement in the wetting times, less foaming, and better suspensibility than certain of the other modified fatty acid or ester adducts of the prior art.

More particularly the tall oil fatty acid or ester anhydride used to make the wetting agent in the improved pesticide formulations may be selected from the group of fatty acids or esters, or mixtures of the same, including linoleic and oleic acid and ester anhydrides, as may be formed by the reaction of oleic or linoleic acids or esters, or other unsaturated fatty acids or esters, with maleic anhydride in a totally aqueous environment. The fatty acid or ester anhydride may contain from about 12 to 20 carbon atoms per molecule. The fatty acid or ester anhydride is reacted with an amino sulfonic acid salt, such as an organic alkyl or aryl salt or sulfamic acid salt. Such sulfonic acid salts include salts of taurine, N-methyl taurine, aminomethanesulfonic acid, 2-aminobenzenesulfonic acid, sulfanilic acid, and sulfamic acid. Particularly good results have been obtained using a sulfamic acid salt.

The reaction of the amino sulfonic acid salt and the fatty acid or ester anhydride is carried out in oil-free aqueous medium over a range of pH values depending on the reactants, as illustrated in specific examples. The reaction temperature required to produce a fatty acid or ester reaction product is between 60° to 100° C., and preferably between about 85° to 95° C.

DETAILED DESCRIPTION OF THE PREFERRED EMBODIMENTS

The present invention may be better understood and explained by reference to the incorporation of the following examples which are given by way of illustration into oil-free pesticide formulations (illustrated later). The three examples given below describe the laboratory production of wetting agents formed from the reaction products of oleic acid ene-anhydride with sulfamic acid, oleic acid ene-anhydride with taurine, and linoleic acid Diels Alder-anhydride/oleic acid ene-anhydride mixture with taurine.

The wetting agent products produced in the following three examples were variously tested for acid number, anionic surfactant activity, and wetting time, and these results were compared with certain commercially available wetting agents of the prior art. The new wetting agents were also tested as a wettable powder addition.

To determine acid number of the wetting agents, approximately one gram of wetting agent was dissolved in 100 mL appropriate solvent (the water-soluble products in water and the water insoluble starting materials in 60%:40% methanol/toluene composition). Phenolphthalein indicator (5 drops) was added, and the solution was titrated with methanolic potassium hydroxide (0.25N) to the end point. The acid number was calculated, as follows:

$$\text{Acid Number} = \frac{(mL\ Titrant)(N\ Titrant)(MW\ Titrant)}{(grams\ sample)}$$

To determine the anionic surfactant activity of the wetting agents, a stock hyamine solution was prepared by washing benzethonium chloride (1.820 grams, 0.004 mol) into a one-liter volumetric flask with distilled water and then taken into solution. The solution was then diluted to the mark on the flask with distilled water giving a 0.004M solution.

Methylene blue indicator solution was prepared by dissolving methylene blue (0.030 gram) in 500 mL distilled water, and concentrated sulfuric acid (6.5 mL) was added. This mixture was diluted to one liter with distilled water and was well mixed.

In making the analysis, approximately one gram of the wetting agent to be analyzed was weighed to the nearest 0.001 gram and dissolved in 50 mL distilled water. It was then transferred to a 100 mL volumetric flask and diluted to the mark on the flask with distilled water. A 2 mL sample of this solution was added to a 100 mL glass-stoppered graduated cylinder, and 25 mL of the methylene blue solution were added. Fifteen (15 mL) milliliters of chloroform were added, and the mixture was titrated with the stock hyamine solution 1-2 mL at a time with 30 second intervals of vigorous shaking. The titration was ended when the aqueous phase was the same shade blue color as the organic phase. The titration volumes were very small as the end point was close. The calculations were made, as follows:

$$\frac{\text{Percent}}{\text{Active Surfactant}} = \frac{5(mL\ Titrant)(N\ Titrant)(MW\ Sample)}{(grams\ sample)}$$

$$\text{Activity Based on Solids} = \frac{\text{Percent Active Surfactant} \times 100\%}{\text{Solids}}$$

Wetting times of the wetting agents were determined by adding the technical pesticide (0.5 grams) to be used to 100 mL volume of the wetting agent as a 2% solution (based on the anionic surfactant activity) and recording the time required for the powder to become completely wet by the aqueous solution. The pH influence on the wetting times was done identically to the regular wetting times with a prior adjustment of the pH of the wetting agent solutions.

EXAMPLE 1

Oleic acid ene-anhydride (11,765 gms, 85% pure, 26.3 mol) was warmed to 60° C. with gentle stirring, and sulfamic acid sodium salt (2,554 gms, 26.3 mol sulfamic acid) in water (5,620 mL, pH adjusted to 12.4 by the addition of 50% sodium hydroxide) was added slowly. The pH was maintained between 2 and 6 (preferably between 5 and 6) throughout the reaction by the addition of 50% sodium hydroxide (3,250 mL) in small increments. The temperature rose 45° C. upon the addition due to the exothermic nature of the reaction taking place. The resulting mixture was allowed to stir at 90° C. for an additional 4 hours, and it was then cooled to give a viscous single phase liquid product. Analysis of the reaction product found the acid number to be 92, the solids content to be 67.8%, and the anionic surfactant activity was assumed to be 50%.

EXAMPLE 2

Oleic acid ene-anhydride (11,765 gms, 85% pure, 26.3 mol) was warmed to 60° C. with gentle stirring, and taurine sodium salt (3,300 gms, 26.4 mol taurine) in water (4,500 mL, pH adjusted to 12.5 by the addition of 50% sodium hydroxide) was added in on portion. The resulting mixture was heated to 90° C. for 6 hours, and it was then cooled to give a viscous single phase liquid product. Analysis of the reaction product found the acid number to be 173, the solids content to be 76.3%, and the anionic surfactant activity to be 36% based on the solids.

EXAMPLE 3

A mixture of the two fatty acid anhydrides (5,000 gms linoleic acid Diels-Alder-anhydride at 70% purity giving 9.26 mol and 5,000 gms oleic acid ene-anhydride at 85% purity giving 11.18 mol) was warmed to 60° C. with gentle stirring, and taurine sodium salt (2,555 gms, 20.44 mol taurine) in water (2,700 mL, pH adjusted to 12 by the addition of 50% sodium hydroxide) was added in one portion. A 12° C. increase in the temperature was noted due to reaction exotherm. The mixture was heated at 92° C. for a total of 36 hours, and it was then cooled to give a viscous single phase liquid product. Analysis of the reaction product found the acid number to be 138, the solids content to be 79.7%, and the anionic surfactant activity to be 55% based on the solids.

TABLE I

EVALUATIONS AND COMPARISONS OF NEW WETTING AGENTS WITH PRIOR ART
Wetting Times and Suspensibilities of Wetting Agents for Atrazine Herbicide:

| Wetting Agent Sample Description | Wetting Time (seconds) | Suspensibility (%) |
| --- | --- | --- |
| Example 1 | 15 | 28 |
| Example 2 | 15 | 100 |
| Example 3 | 30 | 20 |
| Renex 36[1] | 35 | 6 |
| Igepon T-77[2] | 100 | 90 |
| Petro P[3] | 110 | 58 |

[1] A polyoxyethylene ether alcohol from ICI-Americas.
[2] A sodium N-methyl oleotaurate from GAF Corporation.
[3] An alkyl naphthalene sulfonate from DeSoto Chemicals.

Wetting Times for a Broad Spectrum of Technical Pesticides: The wetting times were measured for the three prior art wetting agents, and they were compared with the wetting times for the three example products of the present invention. A broad spectrum of technical grade pesticides were used for this comparison of wetting times. All three of the new wetting agents were found to be competitive with the commercially available wetting agents considered prior art in the area. The results are given in Table II.

TABLE II

| Sample Description | WETTING TIMES (IN SECONDS) FOR PESTICIDES | | | | | | | | | | | | |
|---|---|---|---|---|---|---|---|---|---|---|---|---|---|
| | A[1] | B[2] | C[3] | D[4] | E[5] | F[6] | G[7] | H[8] | I[9] | J[10] | K[11] | L[12] | M[13] |
| Example 1 | 15 | 38 | 20 | 2 | 37 | 300 | 12 | 3 | 3 | 23 | 12 | 4 | 2 |
| Example 2 | 10 | 15 | 20 | 2 | 30 | 300 | 10 | 4 | 7 | 16 | 6 | 5 | 2 |
| Example 3 | 25 | 30 | 45 | 2 | 40 | 300 | 24 | 4 | 8 | 20 | 15 | 9 | 4 |
| Renex 36 | 7 | 35 | 25 | 4 | 15 | 50 | 6 | 3 | 3 | 9 | 45 | 5 | 1 |
| Igepon T-77 | 26 | 100 | 300 | 10 | 300 | 270 | 285 | 25 | 25 | 50 | 30 | 5 | 40 |
| Petro P | 300 | 300 | 120 | 125 | 34 | 300 | 251 | 300 | 12 | 300 | 184 | 5 | 15 |

[1] A = Atrazine A which is from Sipcam
[2] B = Atrazine B which is from I.Pi.Ci.
[3] C = Atrazine C which is from Ciba Geigy.
[4] D = Atrazine D which is from Farmland
[5] E = Cyanizine which is from I. E. DuPont.
[6] F = Simazine which is from Ciba Geigy.
[7] G = Propazine which is from Ciba Geigy.
[8] H = Diuron which is from DuPont.
[9] I = Oxadiazon which is from Rhone-Poulenc.
[10] J = Folpet which is from Chevron.
[11] K = Ziram which is from FMC.
[12] L = Mancozeb which is from FMC.
[13] M = Sulfur which is from Reagent Grade-Aldrich.

The Draves Wetting Test: The Draves wetting test is an evaluation of the efficiency of wetting agents in textile applications. The test is performed by wetting cotton skeins in standard solutions of the wetting agents. The concentrations of the surfactants are based on the activity, and the results are reported in seconds.

TABLE III

| | Temperature | | | | | | | |
|---|---|---|---|---|---|---|---|---|
| | 25° C. Concentration (gms/mL) (Based on Activity) | | | | 50° C. Concentration (gms/mL) (Based on Activity) | | | |
| Wetting Sample Description | 0.50 | 1.25 | 2.50 | 5.0 | 0.50 | 1.25 | 2.50 | 5.0 |
| Example 1 | 74 | 12 | 5 | 3 | 71 | 16 | 6 | 3 |
| Example 2 | 23 | 5 | 2 | 1 | 25 | 7 | 2 | 1 |
| Example 3 | 1800 | 56 | 17 | 7 | 1800 | 62 | 32 | 13 |
| Renex 36 | 16 | 5 | 2 | 1 | 18 | 5 | 2 | 1 |
| Igepon T-77 | 60 | 42 | 21 | 19 | 27 | 15 | 11 | 8 |
| Petro P | 1800 | 58 | 11 | 4 | 1800 | 96 | 10 | 2 |

The maximum allowable time for wetting of the cotton skein is 1800 seconds.

Preparation and Evaluation of the Wettable Powder Formulation: (1) The appropriate wetting agent was combined with REAX 85A (30% wetting agent and 70% lignosulfonate in water with the total solids content of 30%), and the resulting solution was spray dried. (2) The lignosulfonate/wetting agent combinations were combined with atrazine technical herbicide and HiSil in the following proportions:
(3) The mixtures are first mixed in a blender and then air-milled to a small homogeneous particle size. (4)

| Lignin/Wetting Agent | 1.25 grams (5%) |
|---|---|
| Atrazine | 20.50 grams (82%) |
| HiSil | 3.25 grams (13%) |

Evaluations were begun after the air-milled wettable powders were allowed to stand undisturbed in a glass container for 72 hours.

Wetting Times for the Atrazine Wettable Powder Formulation: The wetting times were measured (in seconds) for the atrazine wettable powder formulation in a range of different water hardnesses. These wetting times are illustrated along with the suspensibility characteristics in the following table. The numbers in parenthesis are the suspensibilities in the appropriate water hardness.

TABLE IV

| | WETTING TIMES AND SUSPENSIBILITIES | | | | | | | |
|---|---|---|---|---|---|---|---|---|
| Sample Description | Tap Water | | 342 ppm | | Heated 342 ppm | | 1000 ppm | |
| | Sec. | % | Sec. | % | Sec. | % | Sec. | % |
| 1 | 170 | 92 | 155 | 76 | 142 | 52 | 140 | 50 |
| 2 | 165 | 84 | 135 | 76 | 188 | 86 | 130 | 76 |
| 3 | 165 | 96 | 225 | 78 | 90 | 96 | 165 | 80 |
| Renex 36 | 75 | 100 | 100 | 82 | 135 | 100 | 90 | 80 |
| Igepon T-77 | 90 | 90 | 175 | 78 | 90 | 100 | 105 | 82 |
| Petro P | 285 | 96 | 600 | 84 | 200 | 100 | 345 | 80 |

Wetting times refer to complete wetting of the dry material. Suspensibility is determined by percent of total wettable powders remaining in suspension after 72 hours.

Foaming and Suspensibility Measurements for the Atrazine Wettable Powder: The foaming an suspensibility characteristics were determined for several atrazine wettable powders. The new wetting agents offer low or fast breaking foam, and they have high suspensibilities over the range of water hardnesses. The results are as follows:

TABLE V

| | FOAMING AND SUSPENSIBILITY | | | | | | | | | | | |
|---|---|---|---|---|---|---|---|---|---|---|---|---|
| | Distilled Water | | | | 342 ppm Hard Water | | | | 1000 ppm Hard Water | | | |
| Sample Description | Susp.* | Foaming (cm) Time (min) | | | Susp.* | Foaming (cm) Time (min) | | | Susp.* | Foaming (cm) Time (min) | | |
| | | 0 | 5 | 30 | | 0 | 5 | 30 | | 0 | 5 | 30 |
| 1 | 96% | 2.0 | 1.0 | 0.5 | 76% | 3.0 | 2.0 | 0.5 | 50% | 1.5 | 1.0 | 1.0 |
| 2 | 84% | 1.0 | 0.5 | 0.5 | 76% | — | — | — | 76% | 2.0 | 1.0 | 1.0 |
| 3 | 96% | 3.0 | 2.0 | 0.5 | 78% | 2.0 | 1.0 | 0.5 | 80% | 3.0 | 2.5 | 2.0 |
| Renex 36 | 100% | 6.0 | 5.0 | 5.0 | 82% | 4.5 | 4.5 | 4.0 | 80% | 5.0 | 4.5 | 4.0 |
| Igepon T-77 | 90% | 6.5 | 6.5 | 6.0 | 78% | 6.0 | 5.5 | 5.5 | 82% | 5.5 | 5.5 | 4.0 |
| Petro P | 96% | 1.5 | 1.2 | 1.0 | 84% | 3.0 | 1.5 | 1.5 | 80% | 2.0 | 0.5 | 0.5 |

*Susp. = Suspensibility

The suspensibility and foaming studies were performed by first wetting the various atrazine wettable powders (2 grams each) in the appropriate ionic strength water and then inverting and reverting 30 times in two minutes. The foaming levels were then measured at specific time intervals (0, 5, and 30 minutes). After the last foam reading, a 25 mL portion of the mixture was removed from the center, and it was dried and weighed to give the suspended solids o suspensibility.

Redispersibility of the Atrazine Wettable Powder: The redispersibility measurements relate to the ease at which the formulations break up after the suspended material has settled to the bottom of their containers. The measurement is obtained by first allowing the formulation dispersion to settle to the bottom of the container by standing undisturbed for 72 hours. The mixture is then inverted and reverted until the settlement cake has become redispersed. The number of inversions is then recorded as the redispersibility value.

TABLE VI

REDISPERSIBILITY OF ATRAZINE WETTABLE POWDER

| Sample Description | Tap Water | (number of conversions) 342 ppm Hard Water | | | 1000 ppm Hard Water |
|---|---|---|---|---|---|
| | | Regular | Heated | Slurried | |
| 1 | 15 | 2 | 2 | 1 | 2 |
| 2 | 9 | 8 | 4 | 5 | 12 |
| 3 | 20 | 20 | 20 | 20 | 20 |
| Renex 36 | 20 | 10 | 17 | 9 | 11 |
| Igepon T-77 | 20 | 20 | 20 | 20 | 20 |
| Petro P | 20 | 20 | 20 | 20 | 20 |

Twenty inversions was the cut-off number.

Fertilizer Compatibility Tests for the Atrazine Wettable Powder: In the farmer's continuing efforts to reduce costs, he often combines materials in his spray tank to minimize the number of times he applies materials to the field. A current trend is for farmers to combine the pesticide formulation with fertilizers or micronutrients and apply them simultaneously. Problems are being encountered due to the incompatibility of the pesticide formulation and the fertilizers. This test gives an indication of the wettable powder compatibility with a common fertilizer. The fertilizer compatibility test was performed by mixing the atrazine wettable powder (1 gm in 10 mL of 342 ppm hard water) with 30% nitrogen UAN fertilizer (90 mL). The mixture was inverted and reverted 10 times, and the amount of flocculation was measured at different time intervals. After 30 minutes, the foam height and number of inversions required to break the settlement cake were recorded.

The flocculation is measured by passing the mixture through a 50 mesh screen by gravity filtration and weighing the amount of material trapped on the screen. Slight refers to 0 to 40% of the material caught on the screen as a floc. Moderate refers to 40 to 60% of the material caught on the screen. Heavy refers to greater than 60% of the material caught on the screen.

TABLE VII

FERTILIZER COMPATIBILITY TESTS FOR ATRAZINE WETTABLE POWDERS

| Sample Description | Amount of Flocculation | | | Number of Inversions | Height of Foam (cm) |
|---|---|---|---|---|---|
| | Initial | 15 Min. | 30 Min. | | |
| 1 | Slight | Slight | Slight | 1 | 0.5 |
| 2 | Slight | Moderate | Moderate | 6 | 0 |
| 3 | None | Moderate | Moderate | 1 | 1.0 |
| Renex 36 | None | Moderate | Moderate | 6 | 1.0 |
| Igepon T-77 | None | None | Moderate | 4 | 1.0 |
| Petro P | None | None | Moderate | 3 | 0.5 |

While the invention has been described and illustrated herein by references to various specific materials, procedures and examples, it is understood that the invention is not restricted to the particular materials, combinations of materials, and procedures selected for that purpose. Numerous variations of such details can be employed, as will be appreciated by those skilled in the art.

That which is claimed is:

1. In an aqueous pesticide formulation comprising a dry solid pesticide, a water-soluble dispersant, and an oil-free wetting agent, the improvement comprising, as the oil-free wetting agent, a fatty acid salt produce by reacting a fatty acid anhydride with an animo sulfonic acid salt selected from the group consisting of an organic alkyl salt, an organic aryl salt, and sulfamic acid slat, wherein the fatty acid anhydride is prepared as the reaction product of maleic anhydride and a mixture of tall oil fatty acids comprising oleic acid and linoleic acid.

2. The pesticide formulation of claim 1 wherein the pesticide is selected from the group consisting of herbicides, insecticides, fungicides, and rodenticides.

3. The pesticide formulation of claim 1 wherein the formulation is selected from the group of consisting of emulsifiable concentrates, flowables, wettable powders, and water-dispersible granules.

4. The pesticide formulation of claim 1 wherein the amino sulfonic acid salt is an organic alkyl salt selected from the group of salts of taurine, N-methyl taurine, aminomethanesulfonic acid, and sulfanilic acid.

5. The pesticide formulation of claim 1 wherein the amino sulfonic acid salt is an organic aryl salt form of 2-aminobenzenesulfonic acid.

6. The pesticide formulation of claim 1 wherein the amino sulfonic acid salt is a salt of sulfamic acid.

7. The pesticide formulation of claim 1 wherein the fatty acid anhydride comprises from about 12 to about 20 carbon atoms per molecule.

8. The pesticide formulation of claim 1 wherein the reaction of the fatty acid anhydride with the amino sulfonic acid salt is carried out in an oil-free aqueous medium at a temperature of from about 60° to about 100° C.

9. The pesticide formulation of claim 8 wherein the temperature is from about 85° to about 95° C.

* * * * *

UNITED STATES PATENT AND TRADEMARK OFFICE
CERTIFICATE OF CORRECTION

PATENT NO. : 5,167,694
DATED : December 1, 1992
INVENTOR(S) : Philip L. Robinson It is certified that error appears in the above-indentified patent and that said Letters Patent is hereby corrected as shown below:

In column 4, line 14, delete "on" and substitute therefor --one--.

In column 5, list at line 55 should be after proportions in line 50.

In column 6, line 51, delete "an" and substitute therefor --and--.

In column 7, line 9, delete "o" and substitute therefor --or--.

In Claim 1, column 8, line 26, delete "produce" and substitute therefor --produced--.

In Claim 1, column 8, line 27, delete "animo" and substitute therefor --amino--.

Signed and Sealed this

Twenty-sixth Day of October, 1993

Attest:

BRUCE LEHMAN

*Attesting Officer*

*Commissioner of Patents and Trademarks*